United States Patent
Wilson et al.

(10) Patent No.: US 10,010,639 B2
(45) Date of Patent: Jul. 3, 2018

(54) ELECTRICAL PLUG IN FRAGRANCE DISPENSER HAVING A REMOVABLE DECORATIVE SHEATH

(71) Applicant: Rimports (USA) LLC, Provo, UT (US)

(72) Inventors: Todd Wilson, Orem, UT (US); Tyler Davis, Orem, UT (US); Jeff Goodsell, Springville, UT (US)

(73) Assignee: RIMPORTS, LLC, Provo, UT (US)

( * ) Notice: Subject to any disclaimer, the term of this patent is extended or adjusted under 35 U.S.C. 154(b) by 574 days.

(21) Appl. No.: 14/603,195

(22) Filed: Jan. 22, 2015

(65) Prior Publication Data

US 2016/0213801 A1   Jul. 28, 2016

(51) Int. Cl.
*A61M 16/00* (2006.01)
*F24F 3/14* (2006.01)
*A61L 9/03* (2006.01)

(52) U.S. Cl.
CPC ..................... *A61L 9/03* (2013.01)

(58) Field of Classification Search
None
See application file for complete search history.

(56) References Cited

U.S. PATENT DOCUMENTS

| | | | | |
|---|---|---|---|---|
| 3,780,260 A | * | 12/1973 | Elsner | F21S 8/035 362/101 |
| 3,948,445 A | * | 4/1976 | Andeweg | A01M 1/2066 239/136 |
| 4,344,116 A | * | 8/1982 | Martin | H01R 13/717 362/644 |
| 5,111,477 A | * | 5/1992 | Muderlak | H05B 1/0225 392/390 |
| D346,207 S | * | 4/1994 | Martin | D23/366 |
| D350,209 S | * | 8/1994 | Martin | D26/26 |
| 5,352,122 A | * | 10/1994 | Speyer | F21S 8/035 439/13 |
| 5,375,728 A | * | 12/1994 | West | H02G 3/14 174/488 |
| 5,402,517 A | * | 3/1995 | Gillett | A01M 1/2077 261/DIG. 89 |
| 5,465,198 A | * | 11/1995 | Kellogg | F21S 8/035 362/253 |
| 5,495,402 A | * | 2/1996 | Houssian | F21S 8/035 362/186 |
| 5,634,806 A | * | 6/1997 | Hahn | H01R 27/00 439/172 |
| 5,647,052 A | * | 7/1997 | Patel | A01M 1/2083 392/390 |
| 5,738,540 A | * | 4/1998 | Hetherington | H01R 24/28 174/66 |

(Continued)

Primary Examiner — Thor Campbell
(74) Attorney, Agent, or Firm — Durham Jones & Pinegar, P.C. Intellectual Property Law Group

(57) ABSTRACT

An electrical plug in fragrance dispenser can include a removable decorative sheath. The dispenser can be configured so that, when the sheath is attached, an electrical outlet is completely covered. In this way, the dispenser will have the appearance of a more permanent decorative light fixture. The dispenser can also be configured to plug into two outlets of an electrical receptacle thereby increasing the stability of the dispenser when attached to the wall or other surface. The dispenser may also include an outlet so that the receptacle can still be used when the dispenser is secured overtop the receptacle.

19 Claims, 11 Drawing Sheets

(56) References Cited

U.S. PATENT DOCUMENTS

| | | | | |
|---|---|---|---|---|
| 5,903,710 | A * | 5/1999 | Wefler | A01M 1/2077 239/47 |
| 6,044,202 | A * | 3/2000 | Junkel | A61L 9/03 239/135 |
| 6,104,866 | A * | 8/2000 | DeWitt | A61L 9/03 392/390 |
| 6,104,867 | A * | 8/2000 | Stathakis | A61L 9/037 392/390 |
| 6,123,935 | A * | 9/2000 | Wefler | A61L 9/037 219/201 |
| 6,141,496 | A * | 10/2000 | Sundberg | A61L 9/03 392/390 |
| 6,270,720 | B1 | 8/2001 | Mandish | A61L 9/03 239/60 |
| 6,390,647 | B1 * | 5/2002 | Shaefer | F21S 8/035 362/267 |
| 6,478,440 | B1 * | 11/2002 | Jaworski | A01M 1/04 362/253 |
| 6,714,725 | B2 | 3/2004 | Grone | A01M 1/2077 392/390 |
| 6,859,615 | B2 * | 2/2005 | Yip | A61L 9/037 392/390 |
| 6,862,403 | B2 * | 3/2005 | Pedrotti | A01M 1/2072 392/392 |
| 6,901,215 | B2 * | 5/2005 | He | A01M 1/2072 392/390 |
| D507,844 | S * | 7/2005 | Friedman | D26/118 |
| 7,186,016 | B2 * | 3/2007 | Jao | B44C 5/005 362/101 |
| 7,277,626 | B2 * | 10/2007 | Pesu | A61L 9/037 392/390 |
| 7,398,013 | B2 * | 7/2008 | He | A01M 1/2072 392/390 |
| 7,542,664 | B2 * | 6/2009 | He | A01M 1/2072 392/390 |
| 7,568,829 | B2 * | 8/2009 | Chien | F21S 8/035 362/641 |
| D633,192 | S * | 2/2011 | Valentino | D23/366 |
| 8,135,265 | B2 * | 3/2012 | Tollens | A01M 1/205 392/395 |
| 8,262,277 | B2 * | 9/2012 | Hsiao | A61L 9/03 362/643 |
| 8,651,879 | B2 * | 2/2014 | Stiehl | H01R 13/6658 439/76.1 |
| 9,006,987 | B2 * | 4/2015 | Maxik | F21V 23/06 315/200 R |
| 2004/0005146 | A1 * | 1/2004 | Wefler | A01M 1/2072 392/392 |
| 2004/0057706 | A1 * | 3/2004 | Grone | A01M 1/2077 392/392 |
| 2004/0160769 | A1 * | 8/2004 | Currie | F21S 8/035 362/232 |
| 2005/0201081 | A1 * | 9/2005 | Brady | F21S 8/035 362/101 |
| 2006/0237439 | A1 * | 10/2006 | Norwood | A01M 1/2077 219/506 |
| 2007/0237498 | A1 * | 10/2007 | Helf | A01M 1/205 392/386 |
| 2010/0178042 | A1 * | 7/2010 | Neumann | A01M 1/2077 392/386 |
| 2011/0110118 | A1 * | 5/2011 | Hsiao | A61L 9/03 362/643 |
| 2014/0018285 | A1 * | 1/2014 | D'Amico | C11B 5/0078 512/4 |

* cited by examiner

ELECTRICAL PLUG IN FRAGRANCE DISPENSER HAVING A REMOVABLE DECORATIVE SHEATH

CROSS-REFERENCE TO RELATED APPLICATIONS

Not Applicable.

BACKGROUND

Electrical plug in fragrance dispensers are electrical devices that typically include a light bulb or other heating element for providing heat that melts wax or heats oil containing a fragrance. These dispensers are typically configured to plug into a wall outlet for powering the light bulb or other heating element.

FIG. 1 illustrates an example of a typical prior art electrical plug in fragrance dispenser 100, which is also referred to as a "dispenser" for simplicity. Dispenser 100 includes an electrical housing 101 that is configured to plug into an electrical outlet 110, which is also referred to more simply as an "outlet." Dispenser 100 also includes a decorative component 102 with a bowl-like top surface in which wax or oil is placed. Decorative component 102 is configured to attach to electrical housing 101 so that the decorative component 102 surrounds a light bulb. In the configuration employed by dispenser 100, decorative component 102 extends upwardly from electrical housing 101. However, in other configurations, the decorative component 102 may extend downwardly from the electrical housing 101.

Various problems exist with these typical prior art electrical plug in fragrance dispensers. For example, as is shown in FIG. 1, decorative component 102 is relatively large and heavy. Because of this and the fact that electrical housing 101 is only secured to the wall by the two or three prongs that insert into outlet 110, dispenser 100 can easily be knocked off the wall which may result in the spilling of the heated wax or oil.

For similar reasons, dispenser 100 may sag from outlet 110 which is aesthetically undesirable. Further, as shown in FIG. 1, in prior art dispenser designs, electrical housing 101 and at least portions of outlet 110 remain visible during use of dispenser 100. Therefore, even though decorative component 102 provides some aesthetic benefits, many consumers feel that the overall appearance of the dispenser 100 is unsatisfactory.

Also, in many prior art dispenser designs, the decorative component 102 is not removable from the electrical housing 101. Therefore, if the consumer desires a different decorative design, he or she must discard the entire dispenser 100 rather than being able to replace only the decorative component 102.

BRIEF SUMMARY

The present invention extends to an electrical plug in fragrance dispenser having a removable decorative sheath. The dispenser can be configured so that, when the sheath is attached, an electrical outlet is completely covered. In this way, the dispenser will have the appearance of a more permanent decorative light fixture. The dispenser of the present invention can also be configured to plug into two outlets of an electrical receptacle, thereby increasing the stability of the dispenser when attached to the wall or other surface. The dispenser may also include an outlet so that the receptacle can still be used when the dispenser is secured overtop the receptacle.

In one embodiment, the present invention is implemented as an electrical plug-in fragrance dispenser comprising a housing having a rear surface from which at least one set of electrical prongs extend, a front surface having a socket for receiving a heating element, and opposing side surfaces along which a groove extends. The dispenser also comprises a decorative sheath that includes a coupling component that is configured to slide into the groove to couple the decorative sheath to the housing, thereby positioning the decorative sheath over the housing.

In another embodiment, the present invention is implemented as an electrical plug in fragrance dispenser comprising a housing having a rear surface from which two sets of electrical prongs extend, the two sets of electrical prongs being positioned to allow the two sets of electrical prongs to be inserted into both outlets of a two outlet electrical receptacle, a front surface having a socket for receiving a light bulb, opposing side surfaces, a top surface, a groove that extends along the opposing side surfaces and the top surface, and a bottom surface having an electrical outlet. The dispenser also comprises a decorative sheath that includes a coupling component that is configured to slide into the groove to couple the decorative sheath to the housing, thereby positioning the decorative sheath over the housing.

In another embodiment, the present invention is implemented as an electrical plug in fragrance dispenser comprising a housing having a rear surface from which at least one set of electrical prongs extend to allow the housing to be plugged into at least one outlet of an electrical receptacle, a front surface that includes circuitry for producing heat, opposing side surfaces, and a groove that extends along the opposing side surfaces. The dispenser also comprises a decorative sheath that includes a coupling component that is configured to slide into the groove to couple the decorative sheath to the housing thereby positioning the decorative sheath over the housing.

This summary is provided to introduce a selection of concepts in a simplified form that are further described below in the Detailed Description. This Summary is not intended to identify key features or essential features of the claimed subject matter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION

FIGS. 2A-2G illustrate various views of an exemplary electrical plug in fragrance dispenser 200 in accordance with one or more embodiments of the present invention. Dispenser 200 generally comprises a housing 201 that includes a groove 201a that extends around upper and outer surfaces of the housing 201. As will be further described below, a decorative sheath can be coupled to housing 201 using a coupling component 203 that slides into groove 201a.

Figure 1:
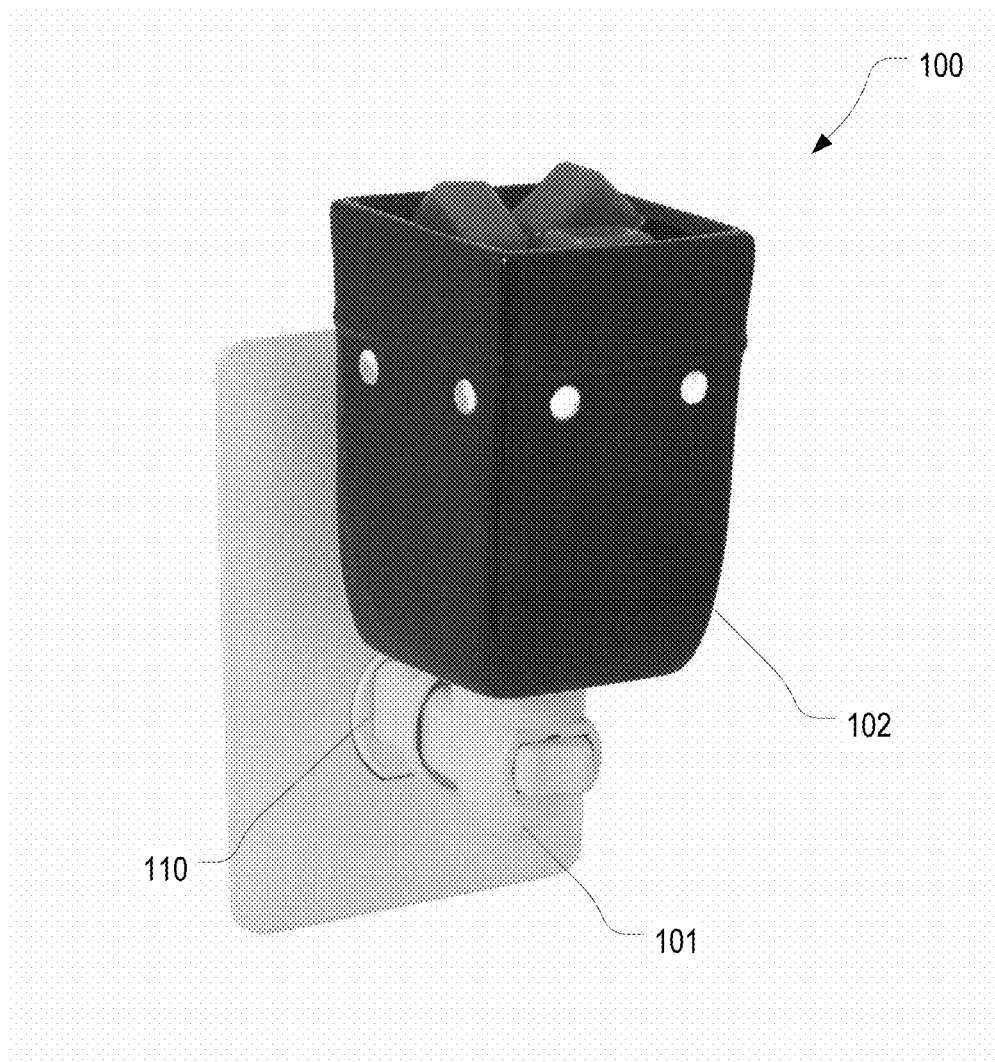
FIG. 1 illustrates an example prior art electrical plug in fragrance dispenser.
Figure 2A:
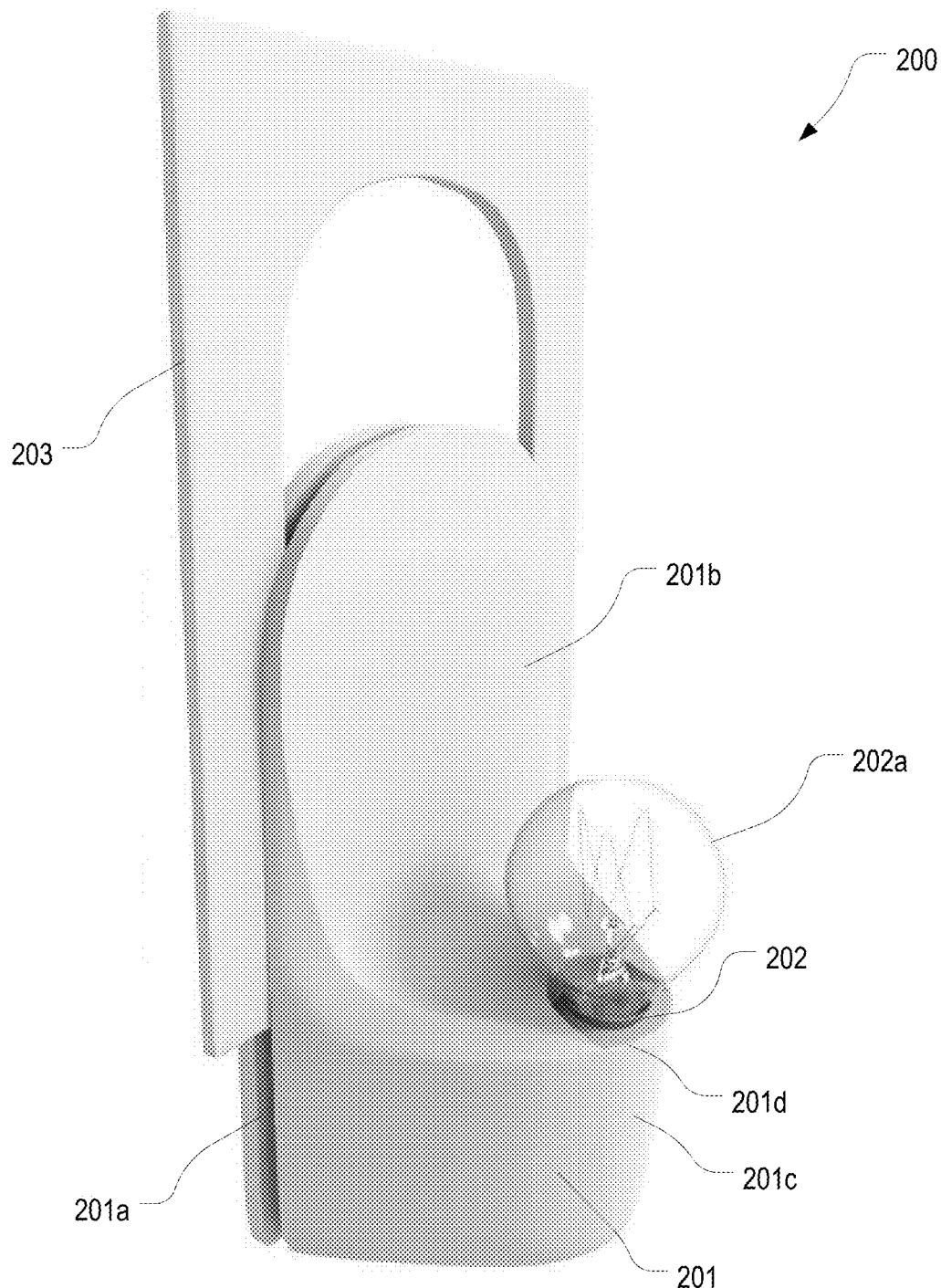
FIG. 2A illustrates a front perspective view of an electrical plug in fragrance dispenser in accordance with one or more embodiments of the present invention.

FIG. 2A provides a front perspective view of dispenser 200. As shown, groove 201a is configured to receive coupling component 203 by which a decorative sheath can be secured to the housing 201 as will be further described below with reference to FIGS. 3A and 3B. In FIG. 2A, coupling component 203 is shown partially inserted into groove 201a to illustrate how the coupling component 203 can be slid into the groove 201a. Housing 201 also includes a light bulb socket 202, which is also more simply referred to as a "socket," that allows a light bulb 202a to be secured to the housing 201.

Housing 201 includes a generally flat portion 201b that extends vertically from a protruding portion 201c. In some embodiments, such as is shown in FIG. 2A, protruding portion 201c can include a recessed portion 201d in which socket 202 is positioned. In some embodiments, the transition between protruding portion 201c and flat portion 201b can be curved as shown in FIG. 2A.

Figure 2B:
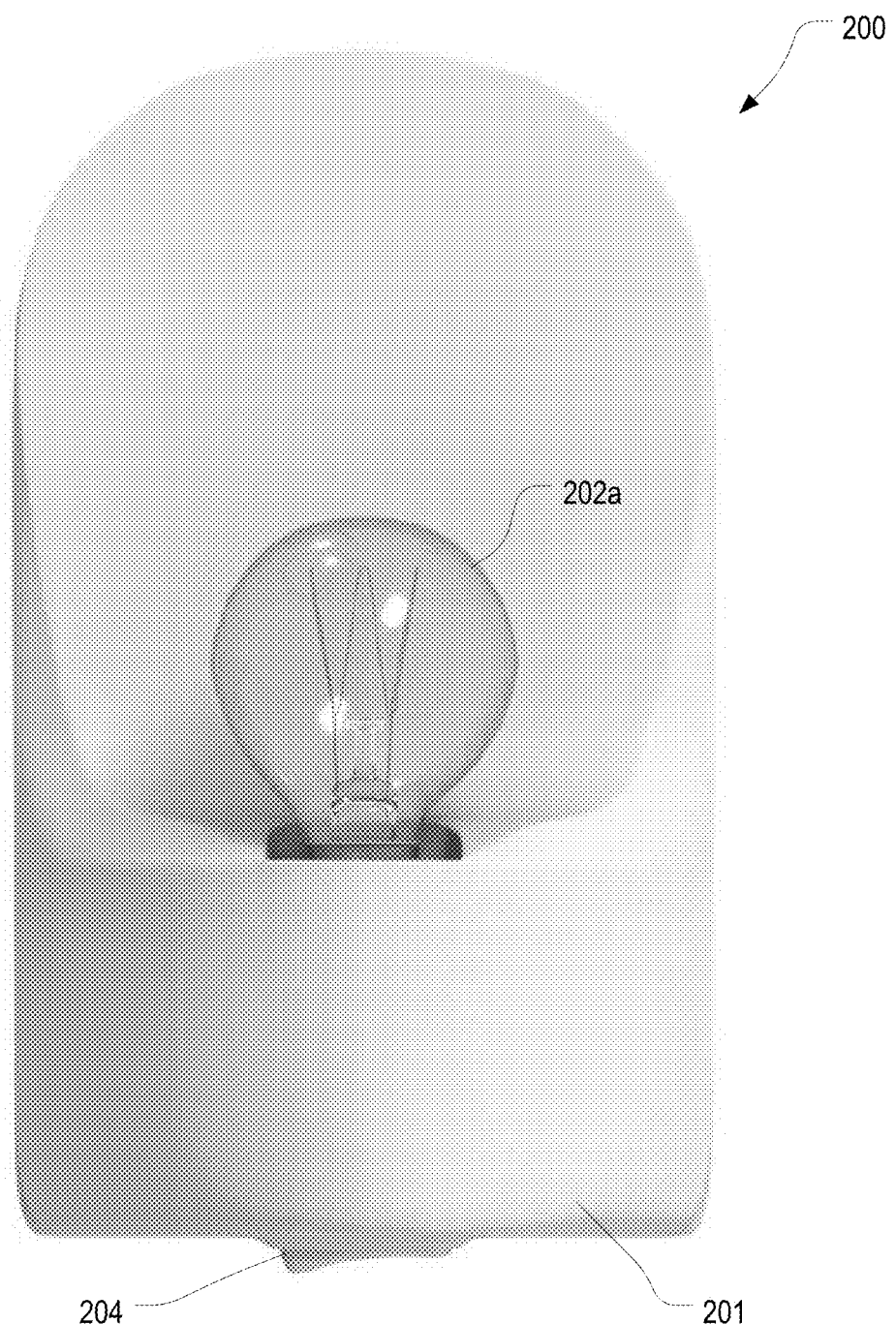
FIG. 2B illustrates a front view of the dispenser of FIG. 2A.

FIG. 2B provides a front view of dispenser 200. Housing 201 can include a switch for operating light bulb 202a. As shown in FIG. 2B, a switch 204 is provided on a bottom surface of housing 201. Providing a switch 204 on the bottom surface of housing 201 can be preferred in many embodiments since the decorative sheath may cover the remaining portions of housing 201. In FIG. 2B, housing 201 is shown without coupling component 203.

Figure 2C:
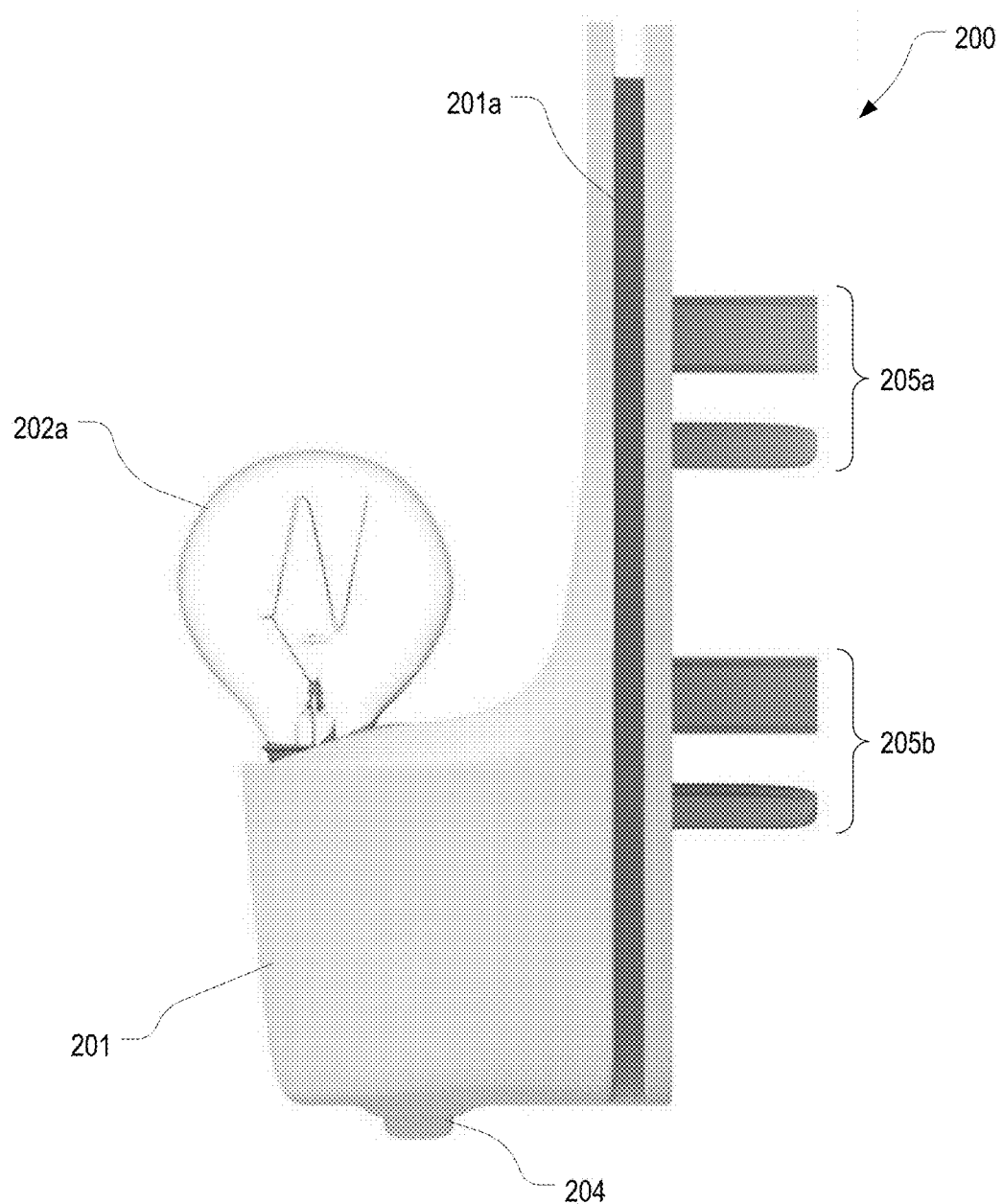
FIG. 2C illustrates a side view of the dispenser of FIG. 2A.

FIG. 2C provides a side view of dispenser 200 which illustrates that housing 201 incorporates two sets of prongs 205a, 205b which are configured to be inserted into both outlets of a standard electrical receptacle. Because housing 201 includes two sets of prongs 205a, 205b, the housing 201 can be more securely fixed to a wall or other surface. Unlike prior art dispenser designs which only provide a single set of prongs 205a, 205b, dispenser 200 therefore spreads the load caused by a decorative sheath or other decorative component between the two outlets. Also, by using two sets of prongs 205a, 205b, there is not a single connection point about which the housing 201 will pivot thereby reducing the likelihood that dispenser 200 will sag from the wall.

In some embodiments, one or both of prongs 205a, 205b may be adjustable to change the distance between the two sets of prongs 205a, 205b thereby allowing dispenser 200 to be plugged into outlets of different sizes. For example, prongs 205a can be configured to be slidable in a vertical direction to adapt to different spacings between outlets. In some embodiments, one of prongs 205a, 205b can be configured as a dummy prong with the other prong providing power to socket 202.

Figure 2D:
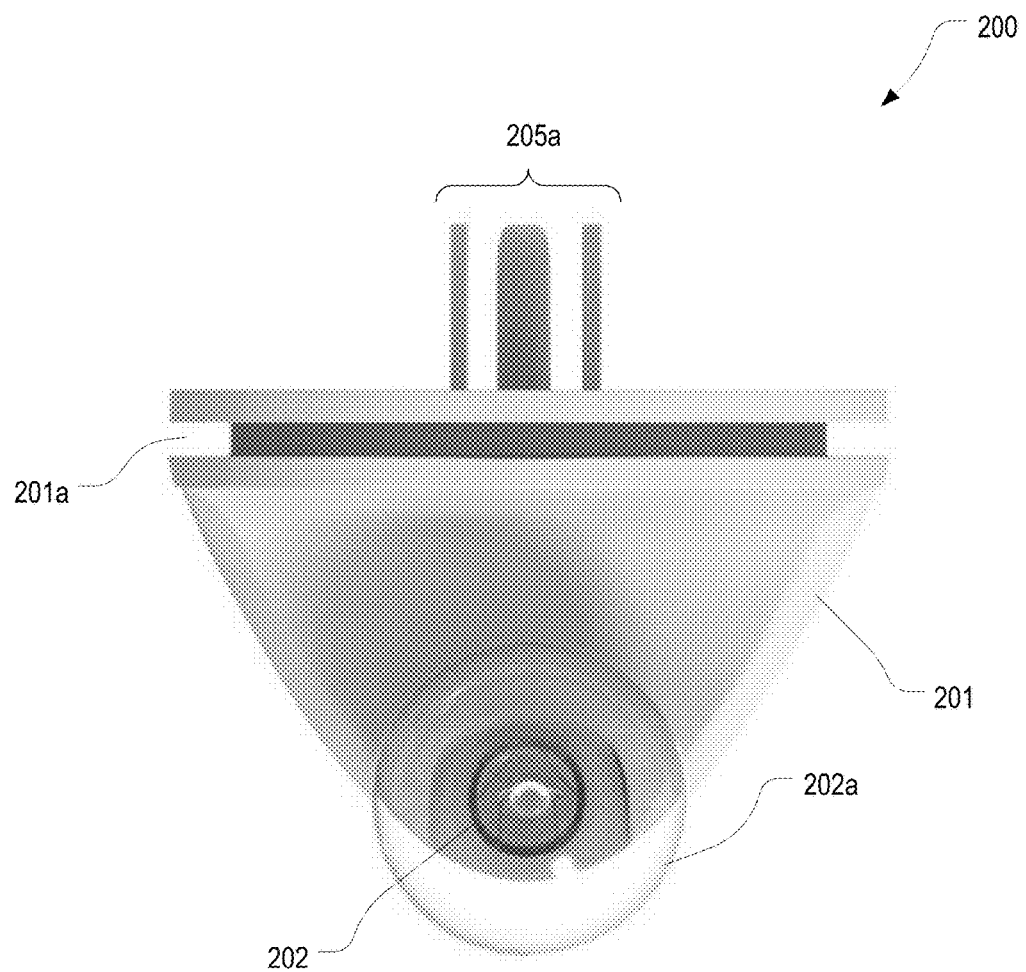
FIG. 2D illustrates a top view of the dispenser of FIG. 2A.

FIG. 2D provides a top view of dispenser 200. As shown, groove 201a can extend fully around the top surface and outside surfaces of housing 201. Therefore, when coupling component 203 is slide fully into groove 201a, groove 201a will provide structural support along three edges of the coupling component 208 to ensure that a decorative sheath is securely fixed to the housing 201 as will be further described below.

Figure 2E:
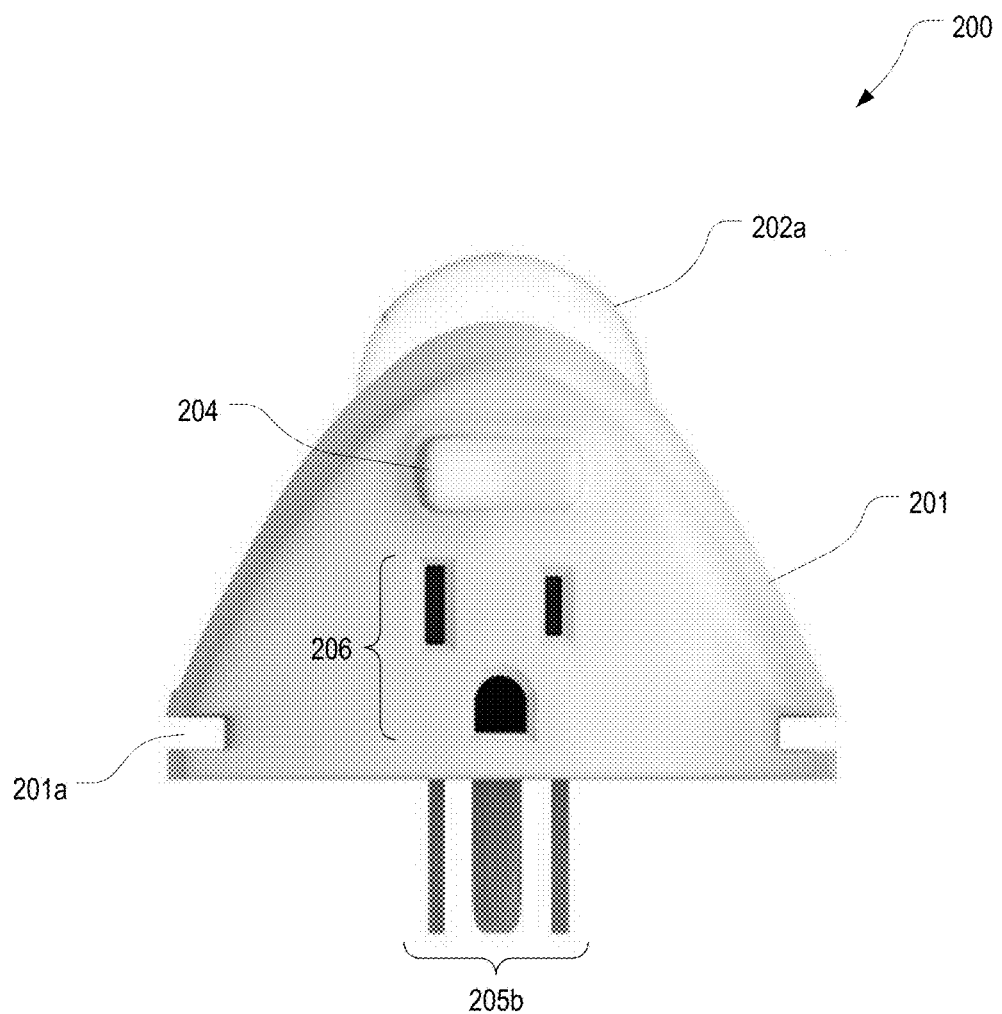
FIG. 2E illustrates a bottom view of the dispenser of FIG. 2A.

FIG. 2E provides a bottom view of dispenser 200 which illustrates that housing 201 can include an outlet 206. By providing outlet 206, dispenser 200 does not prevent a receptacle from being used while the dispenser 200 is plugged into the receptacle. Housing 201 can include suitable electrical components to interconnect one of prongs 205a, 205b with outlet 206 while connecting the other of prongs 205a, 205b to socket 202.

Figure 2F:
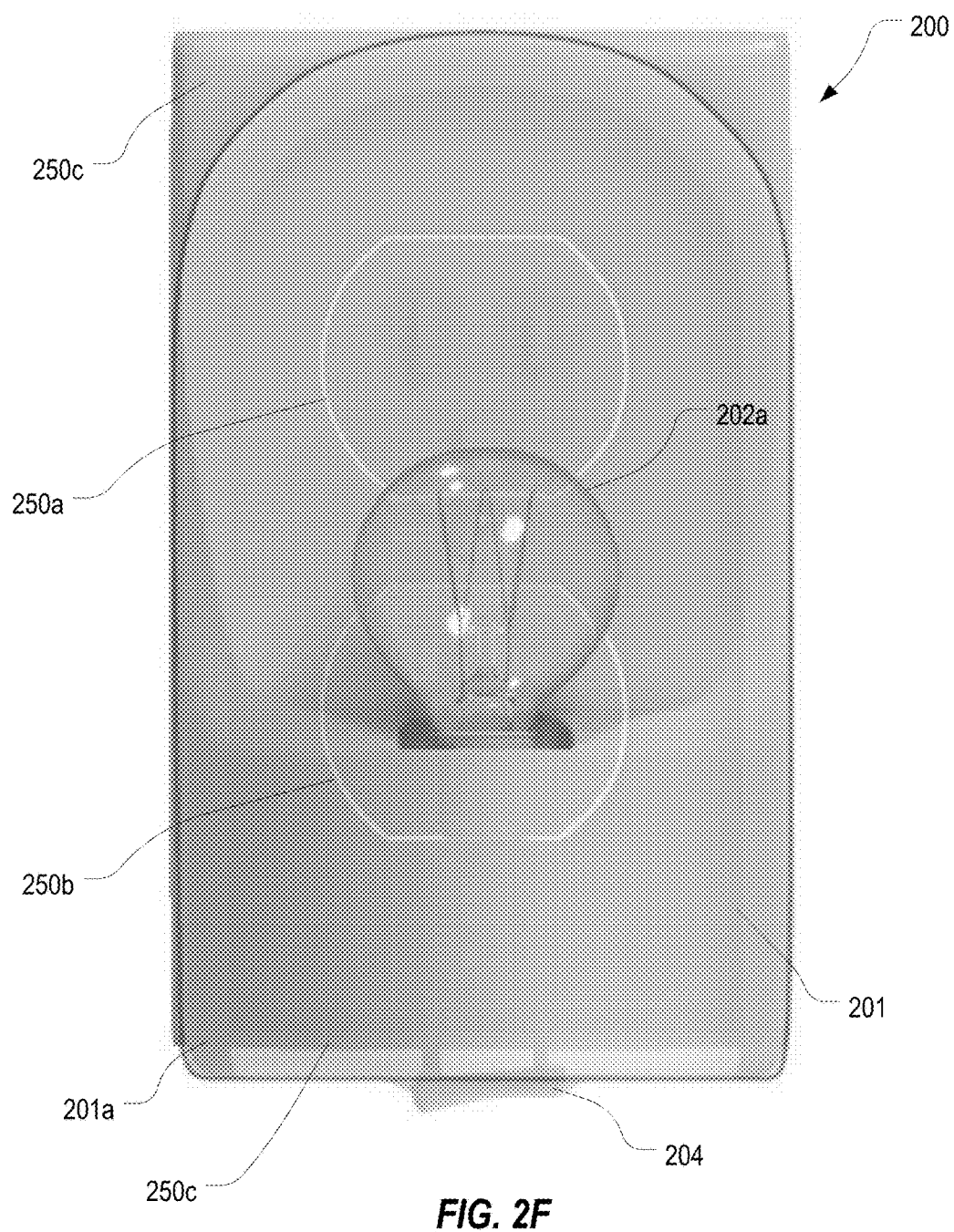
FIG. 2F illustrates a front, semi-transparent view of the dispenser of FIG. 2A.

FIG. 2F provides a semi-transparent front view of dispenser 200 when coupling component 203 is not inserted into groove 201a and while dispenser 200 is plugged into a standard receptacle. The semi-transparent view allows outlets 250a, 250b and a bottom edge of a wall plate 250c to be visible. Top corners of wall plate 250c are also visible due to the rounded surface of housing 201. As shown, the size of housing 201 can be configured such that wall plate 250c is substantially covered. For example, the height of housing 201 can be approximately 4.5 inches and the width can be approximately 2.6 inches so that housing 201 will cover a standard 1 gang wall plate.

Coupling component 203 can have a greater height and width than housing 201 so that the wall plate 250c is fully covered. For example, in some embodiments, coupling component 203 can have a height of approximately 5 inches and a width of approximately 3.5 inches so that the coupling component 203 (or, more particularly, the decorative sheath that the coupling component 203 secures to the housing 201) can fully cover both standard and jumbo 1 gang wall plates. In this way, dispenser 200 can appear as an aesthetically pleasing lighting fixture rather than as a device plugged into an outlet. Of course, any other suitable size and/or shape of dispenser 200 could also be provided to cover wall plates 250c of different sizes and configurations. Sizes and shapes that do not cover the wall plate 250c can also be provided.

Figure 2G:
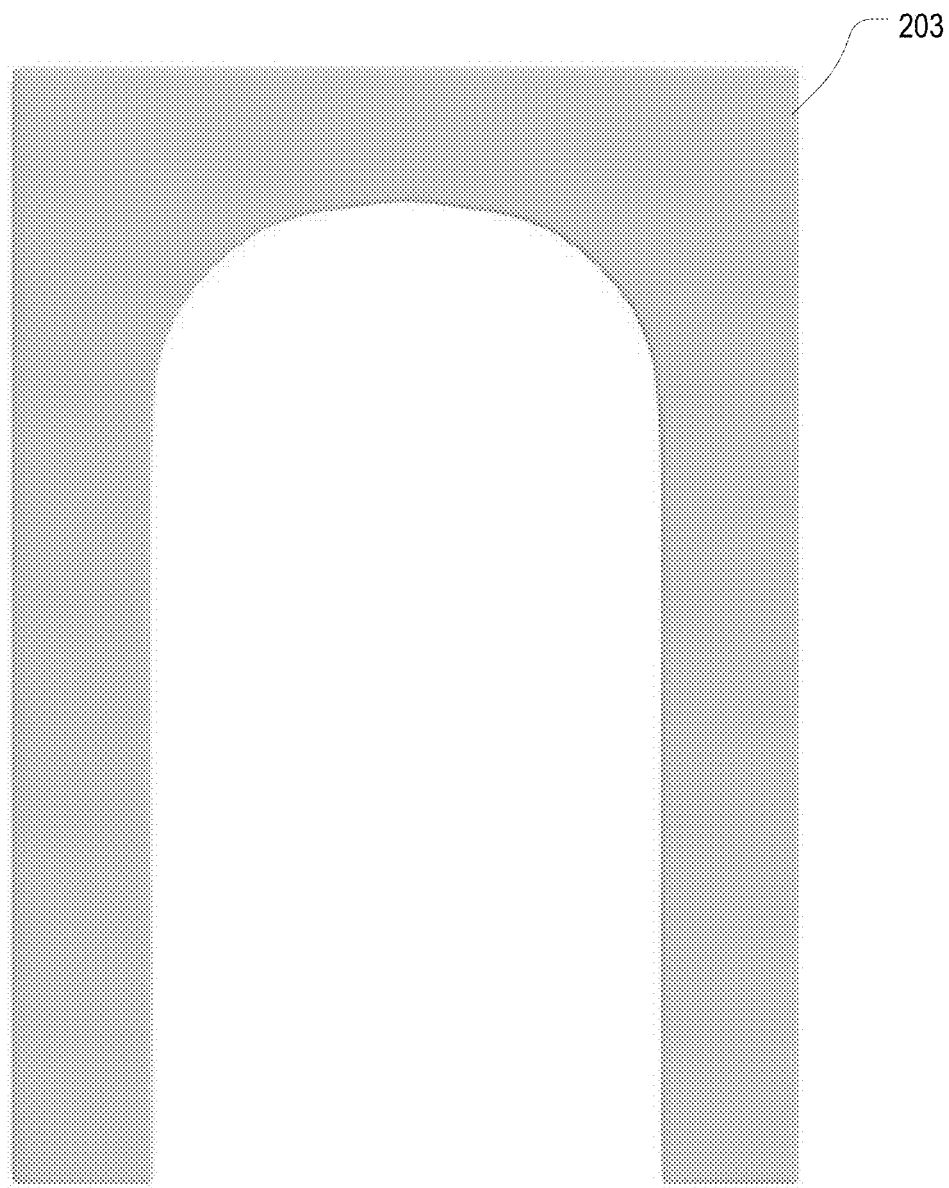
FIG. 2G illustrates a coupling component that can be included a decorative sheath to allow the sheath to be attached to the dispenser of FIG. 2A.

FIG. 2G illustrates a coupling component 203. As shown, coupling component 203 has an inner shape that conforms to the shape of groove 201a. Coupling component 203 can have a thickness that is slightly less than the thickness of groove 201a so that coupling component 203 is snuggly held within the groove 201a while also allowing coupling component 203 to be slid within the groove 201a when necessary (e.g., when removing a decorative sheath). Alternatively or additionally, coupling component 203 may include one or more protrusions or other structures which interlock with corresponding structures within or along groove 201a. For example, one or more protrusions may be formed on a surface of coupling component 203 which snap into corresponding one or more recesses within groove 201a once coupling component 203 has been fully slid into groove 201a.

In some embodiments, the thickness of coupling component 203 may be reduced to allow coupling component 203 to slide easily within groove 201a which may facilitate removal of a decorative sheath from housing 201. For example, it may be desirable to allow a decorative sheath to be removed while containing hot wax, oil, or another substance. In such cases, minimizing the friction between coupling component 203 and groove 201a (e.g., by configuring coupling component 203 with a smaller thickness than groove 201a) can minimize the likelihood that the hot substance will be spilled during removal of the sheath. In such embodiments, interlocking structures can preferably be provided to better secure coupling component 203 to housing 201 when fully inserted into groove 201a.

Figure 3A:
FIG. 3A illustrates a front perspective view of a decorative sheath that can be used with the dispenser of FIG. 2A.

FIG. 3A illustrates a front perspective view of a decorative sheath 300, which may also be referred to as a "sheath," that can be coupled to housing 201. Decorative sheath 300 includes a decorative outer surface 301 and a dish-shaped top surface 302 in which wax, oil, or another fragrance-containing substance may be placed. Decorative sheath 300 is hollow to allow it to be inserted overtop housing 201. In this way, light bulb 202 can act as a heat source for releasing fragrance from the substance placed within the top surface 302 of the sheath 300.

Figure 3B:
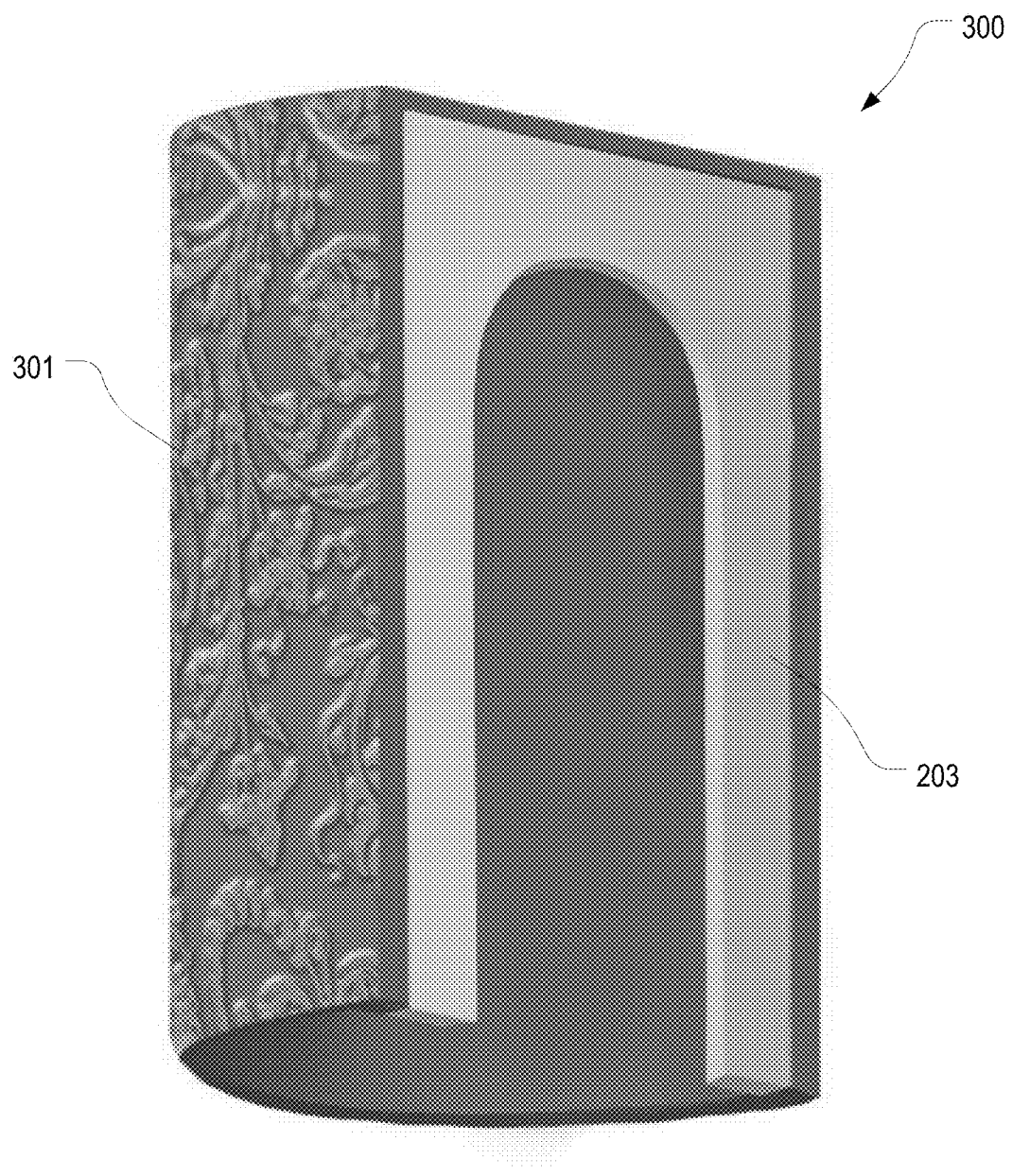
FIG. 3B illustrates a rear perspective view of the decorative sheath of FIG. 3A.

FIG. 3B illustrates a rear perspective view of decorative sheath 300. As shown, sheath 300 can incorporate coupling component 203 to allow decorative sheath 300 to be coupled to housing 201. For example, when coupling component 203 is secured within decorative sheath 300, the coupling component 203 can be slid into groove 201a as is shown in FIG. 2A. In some embodiments, coupling component 203 can be integrally formed into decorative sheath 301. Alternatively, coupling component 203 can be a separate component that is coupled to decorative sheath 301 (e.g., by sliding the coupling component 203 into grooves 201a on the inside surface of the sheath 300, by snapping the coupling component 203 into a retaining structure on the inside surface of the sheath 300, etc.).

Coupling component 203 is positioned along the back surface of decorative sheath 300 so that the decorative sheath 300 will be near or against the wall or other surface when the coupling component 205 is inserted into groove 201a. In some embodiments, coupling component 203 may be spaced a small distance from the back surface of decorative sheath 300 to ensure that the back surface of decorative sheath 300 is positioned against the wall. For example, this small distance can be approximately equal to the combined thickness of the back wall of groove 201a and a standard wall plate.

Figure 4:
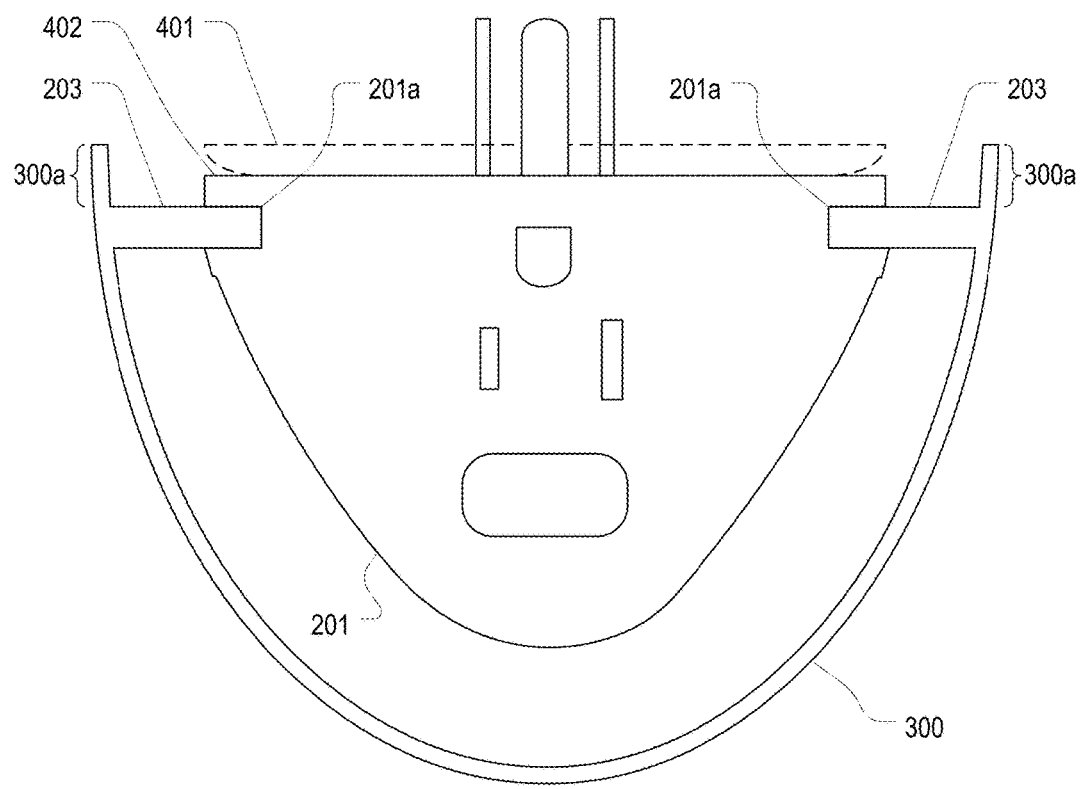
FIG. 4 illustrates how a coupling component can be spaced from a rear surface of a decorative sheath.

FIG. 4 provides an example of how a coupling component 203 can be positioned a small distance from the back edge of decorative sheath 300. FIG. 4 is a bottom view of dispenser 200 when decorative sheath 300 is attached to housing 201 and includes a wall plate 401 shown in dashed lines. As shown, coupling component 203 is positioned a small distance from a rear surface of decorative sheath 300. This distance is approximately equal to the combined thickness of the back wall of groove 201a (labeled as 402) and wall plate 401. Positioning coupling component 203 in this manner will cause a portion 300a of decorative sheath 300 to extend beyond the back surface of housing 201 so that the portion 300a is adjacent to a wall or other surface when housing 201 is plugged into a receptacle in the wall or other surface. This can allow decorative sheath 300 to be flush with the wall to make it appear as though dispenser 200 is a fixture or sconce.

Dispenser 200 is only one example of an electrical plug in fragrance dispenser that is configured in accordance with the present invention. Dispensers of other shapes and sizes can also be provided. For example, a housing can be configured with different shaped and/or sized protruding and flat portions from what is shown in the figures. In short, the present invention should extend to any electrical plug in fragrance dispenser that includes a groove for receiving a coupling component to secure a decorative sheath to the housing and/or two sets of prongs for securing the dispenser to the wall or other structure.

Additionally, in some embodiments, a housing may include a groove that does not extend along a top surface of the housing. For example, groove 201a may be configured to only extend along the opposing sides of the housing. Also, in some embodiments, groove 201a may not extend the full length of the sides.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description.

What is claimed:

1. An electrical plug-in fragrance dispenser comprising:
    a housing having
        a rear portion from which at least one set of prongs capable of being received by a socket of an electrical outlet protrudes;
        a front portion having a socket for receiving a heating element; and
        a pair of oppositely facing side surfaces, with a groove recessed within and extending along a height of each side surface of the oppositely facing side surfaces; and
    a decorative sheath that includes a pair of opposed coupling components, with each coupling component of the pair of opposed coupling components being capable of sliding into a corresponding groove in a corresponding side surface of the oppositely facing side surfaces to couple the decorative sheath to the housing and to position the decorative sheath over the front portion of the housing, including the socket.

2. The electrical plug-in fragrance dispenser of claim 1, wherein a rear surface of the rear portion of the housing is substantially flat.

3. The electrical plug-in fragrance dispenser of claim 2, wherein the at least one set of prongs capable of being received by a socket of an electrical outlet protrudes from the rear surface of the rear portion of the housing.

4. The electrical plug-in fragrance dispenser of claim 1, wherein two sets of prongs capable of being received by both sockets of a two socket electrical outlet protrude from the rear surface of the rear portion of the housing to enable the housing to be secured to both sockets of the two socket electrical outlet.

5. The electrical plug-in fragrance dispenser of claim 4, wherein one set of prongs of the two sets of prongs comprises a dummy set of prongs capable of being received by a socket of the two socket electrical outlet.

6. The electrical plug-in fragrance dispenser of claim 1, wherein the heating element is a light bulb.

7. The electrical plug-in fragrance dispenser of claim 1, wherein the housing includes a top surface continuous with the pair of oppositely facing side surfaces.

8. The electrical plug-in fragrance dispenser of claim 7, wherein a groove is recessed in the top surface.

9. The electrical plug-in fragrance dispenser of claim 8, wherein the groove recessed in the top surface is continuous with the groove in each side surface of the pair of oppositely facing side surfaces.

10. The electrical plug-in fragrance dispenser of claim 1, wherein the coupling component comprises rear edges of the decorative sheath.

11. The electrical plug-in fragrance dispenser of claim 1, wherein the decorative sheath includes a fragrance reservoir.

12. The electrical plug-in fragrance dispenser of claim 11, wherein the fragrance reservoir is removable from the decorative sheath.

13. The electrical plug-in fragrance dispenser of claim 11, wherein the fragrance reservoir includes a lid capable of covering the fragrance reservoir and of being removed from the fragrance reservoir.

14. The electrical plug-in fragrance dispenser of claim 1, wherein the housing further includes an electrical socket in a bottom surface of the front portion of the housing.

15. The electrical plug-in fragrance dispenser of claim 1, wherein the housing further includes a switch associated with the socket.

16. The electrical plug-in fragrance dispenser of claim 1, wherein the rear portion of the housing and the decorative sheath include interlocking features capable of securing the decorative sheath to the housing.

17. The electrical plug-in fragrance dispenser of claim 1, wherein the decorative sheath is capable of laterally surrounding an entirety of the front portion of the housing.

18. The electrical plug-in fragrance dispenser of claim 1, wherein the decorative sheath is capable of covering a top of the front portion of the housing.

19. An electrical plug-in fragrance dispenser comprising:
a housing having:
a rear surface from which two sets of electrical prongs extend, the two sets of electrical prongs being positioned to allow the two sets of electrical prongs to be inserted into both outlets of a two outlet electrical receptacle;
a front surface having a socket for receiving a light bulb;
opposing side surfaces;
a top surface;
a groove that extends along the opposing side surfaces and the top surface; and a bottom surface having an electrical outlet; and
a decorative sheath that includes a coupling component that is configured to slide into the groove to couple the decorative sheath to the housing thereby positioning the decorative sheath over the housing.

* * * * *